(12) United States Patent
Ovcharchyn et al.

(10) Patent No.: US 8,177,773 B2
(45) Date of Patent: May 15, 2012

(54) LOCKING MEDICAL CATHETER

(75) Inventors: Stephen Ovcharchyn, Naperville, IL (US); Richard Hannah, Vista, CA (US)

(73) Assignee: Uresil, LLC, Skokie, IL (US)

( * ) Notice: Subject to any disclaimer, the term of this patent is extended or adjusted under 35 U.S.C. 154(b) by 473 days.

(21) Appl. No.: 12/363,984

(22) Filed: Feb. 2, 2009

(65) Prior Publication Data
US 2009/0247990 A1 Oct. 1, 2009

Related U.S. Application Data

(60) Provisional application No. 61/040,519, filed on Mar. 28, 2008.

(51) Int. Cl.
*A61M 25/18* (2006.01)
*A61M 39/00* (2006.01)
*A61M 39/10* (2006.01)
*A61M 1/00* (2006.01)

(52) U.S. Cl. ........................................ 604/540; 604/533

(58) Field of Classification Search ............. 604/27–29, 604/93.01–95.04, 264, 523, 533, 540
See application file for complete search history.

(56) References Cited

U.S. PATENT DOCUMENTS

| 4,600,402 | A |   | 7/1986 | Rosenberg |   |
|---|---|---|---|---|---|
| 4,643,720 | A |   | 2/1987 | Lanciano |   |
| 4,846,175 | A |   | 7/1989 | Frimberger |   |
| 4,869,719 | A |   | 9/1989 | Hogan |   |
| 5,030,204 | A |   | 7/1991 | Badger et al. |   |
| 5,041,085 | A |   | 8/1991 | Osborne et al. |   |
| 5,100,385 | A | * | 3/1992 | Bromander | 604/99.03 |
| 5,185,004 | A |   | 2/1993 | Lashinski |   |
| 5,352,198 | A |   | 10/1994 | Goldenberg et al. |   |
| 5,399,165 | A |   | 3/1995 | Paul, Jr. |   |
| 5,419,764 | A |   | 5/1995 | Roll |   |
| 5,514,112 | A |   | 5/1996 | Chu et al. |   |
| 5,522,400 | A |   | 6/1996 | Williams |   |
| 5,730,724 | A |   | 3/1998 | Plishka et al. |   |
| 5,810,803 | A | * | 9/1998 | Moss et al. | 606/33 |
| 5,928,208 | A |   | 7/1999 | Chu et al. |   |

(Continued)

FOREIGN PATENT DOCUMENTS

WO    WO 96/34560 A1    11/1996

OTHER PUBLICATIONS

Skater Drainage Catheters, Ver. 7552/53, Angiotech, PBN Medicals Denmark A/S, www.pbn-medicals.com.

(Continued)

*Primary Examiner* — Tatyana Zalukaeva
*Assistant Examiner* — Philip R Wiest
(74) *Attorney, Agent, or Firm* — Drinker Biddle & Reath LLP (57) ABSTRACT

A flexible filament controlled locking medical catheter having a flexible tube with at least one drainage or feeding hole, a restraining portion at its distal end and a housing at its proximal end, and a filament having a proximal control portion for controlling the restraining portion of the tube. The flexible filament passes through an open port in the sidewall of the housing and an elastomeric cover as well as through the interface between the cover and a seal sleeve over the cover. A locking mechanism to lock the filament in position is provided and may comprise corresponding teeth with means for moving the teeth into tight engagement to clamp the flexible filament therebetween.

20 Claims, 10 Drawing Sheets

U.S. PATENT DOCUMENTS

| | | | |
|---|---|---|---|
| 5,941,849 | A | 8/1999 | Amos, Jr. et al. |
| 5,989,241 | A * | 11/1999 | Plishka et al. ............ 604/540 |
| 6,042,577 | A | 3/2000 | Chu et al. |
| 6,159,177 | A | 12/2000 | Amos, Jr. et al. |
| 6,231,542 | B1 | 5/2001 | Amos, Jr. et al. |
| 6,508,789 | B1 | 1/2003 | Sinnott et al. |
| 6,673,060 | B1 | 1/2004 | Fleming, III |
| 6,699,233 | B2 | 3/2004 | Slanda et al. |
| 7,087,038 | B2 | 8/2006 | Lee |
| 7,217,256 | B2 * | 5/2007 | Di Palma ............ 604/104 |
| 2003/0181854 | A1 | 9/2003 | Sauvageau |
| 2004/0039339 | A1 | 2/2004 | Magnusson |

OTHER PUBLICATIONS

Skater Single Step Drainage Sets, Ver. 7565, Angiotech, PBN Medicals Denmark A/S, www.pbn-medicals.com.

Radiology procudts from Angiotech/PBN: Drainage, published on internet web site: http://www.pbn-medicals.com/products/rad_drainage.html (Jan. 13, 2009).

Skater Single Step Drainage Set—Locking, Guidance for Use pamphlet, Ver. 7565-p4, Angiotech, PBN Medicals Denmark A/S, www.pbn-medicals.com.

* cited by examiner

LOCKING MEDICAL CATHETER

CROSS-REFERENCE TO RELATED PATENT APPLICATIONS

This patent application claims the benefit of U.S. Provisional Patent Application No. 61/040,519, filed Mar. 28, 2008.

FIELD OF THE INVENTION

The present invention relates generally to medical catheters designed to be removably anchored within a body cavity by maintaining a restraining configuration controlled by a flexible filament until it is desired to withdraw the catheter from the cavity. More particularly, this invention relates to such locking medical catheters having a unique system for sealing the flexible filament that controls the restraining configuration and for easily and reliably locking and unlocking the flexible filament.

BACKGROUND OF THE INVENTION

Medical catheters are widely used for percutaneous drainage of fluid from body cavities. For example, such catheters may be used in percutaneous nephrostomy, and for drainage of abscesses, bile, cysts, pleural effusions, empyemas, mediastinal collections and ascites. Percutaneously inserted catheters are also used as gastrostomy feeding tubes. In these and similar drainage and feeding applications, the catheters are typically inserted over a previously emplaced guide wire or by direct puncture and insertion using a trocar stylus. Once in position in the body cavity with the proximal end of the catheter protruding from the body, such catheters typically are anchored by forming and maintaining a restraining configuration at the distal end of the catheter in the shape of a pigtail, a J-curve, or a malecot rib. It is very advantageous to include a locking mechanism near the proximal end of the catheter for reliably locking and unlocking the distal restraining portion by manipulating a flexible filament that controls the restraining portion from an access point where the catheter protrudes from the body.

Many known catheter anchoring systems include flexible filaments like suture attached to the distal ends of the catheters to form and maintain the distal end of the catheters in a restraining configuration. Such catheter anchoring systems include locking mechanisms at the proximal ends of the catheters to releaseably hold the suture or other flexible filament in a desired drawn-up restraining position. Currently available locking mechanisms in these catheter anchoring systems comprise, for example, stopcock-type locking mechanisms, flexible sleeve configurations to cover and restrain the suture, locking bushings, and various complex clamping structures.

Prior catheter anchoring systems are described, for example, in U.S. Pat. Nos. 4,643,720 and 4,740,195. These anchoring systems use a stopcock feature to capture the suture that controls the restraining configuration of the catheter within the lumen of the catheter. The end of the suture exits the catheter directly through a proximal housing.

There are several problems associated with this system. First, in order to lock and unlock the system, the operator is required to use a special key device provided with the system. Unfortunately, when it comes time to remove the catheter, this key device may no longer be available and so the user will have to find a suitable tool that will properly function in lieu of the missing key device. Second, the positioning of the suture within the lumen of the housing is problematic. In particular, because the suture exits the proximal housing, it frequently ends up crossing the threaded interface between the catheter housing and the drainage device that the catheter is attached to. For example, when such catheters are attached to drainage collection bags, the presence of the suture across the threaded interface can cause leakage across the interface that is unpleasant for the patient and can create contamination risks for individuals who come in contact with the patient and/or the device.

Another commonly used catheter anchoring system is described in U.S. Pat. No. 5,399,165. This system utilizes a hinged lever with a cam feature to restrain the suture holding the restraining configuration of the catheter in place. Like the above device, this locking system cannot be unlocked without the use of a tool that needs to be identified and procured by the health care professional attempting to unlock the system.

The system of the present invention requires no special tools for locking or unlocking. The user locks the system by moving a permanently mounted locking slide into a proximal position. To unlock the system, the user depresses a latch and moves the locking slide distally. Also, there is no leakage due to suture position since the free proximal control portion of the suture (flexible filament) that controls the restraining portion of the catheter exits the catheter lumen through a unique elastomeric cover positioned on the sidewall of the device and a seal sleeve which together ensure leakage-free operation. Also, since the suture does not pass through the proximal luer lock, it cannot interfere with the threaded interface to the collection device.

Figure 1:
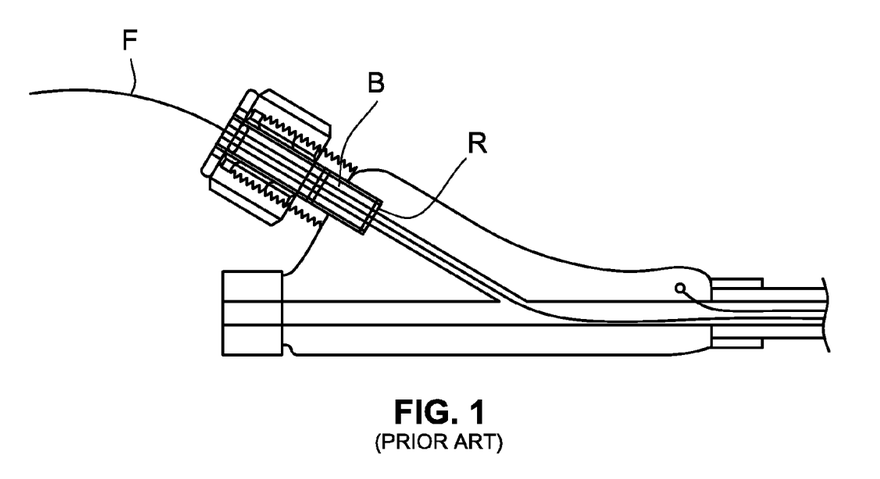
FIGS. 1-4 depict portions of prior art locking medical catheters and a urinary drainage bag sampling port.

A prior art locking catheter system described in U.S. Pat. No. 5,522,400, assigned to the present assignee, is illustrated in FIG. 1. In this locking catheter system a flexible filament F passes through a compressible bushing B made of a conventional deformable sealing material like silicone. This bushing is disposed in a recess R in the housing of the device. When compressed, the bushing locks the flexible filament in place while maintaining a liquid and gas seal.

Figure 2:
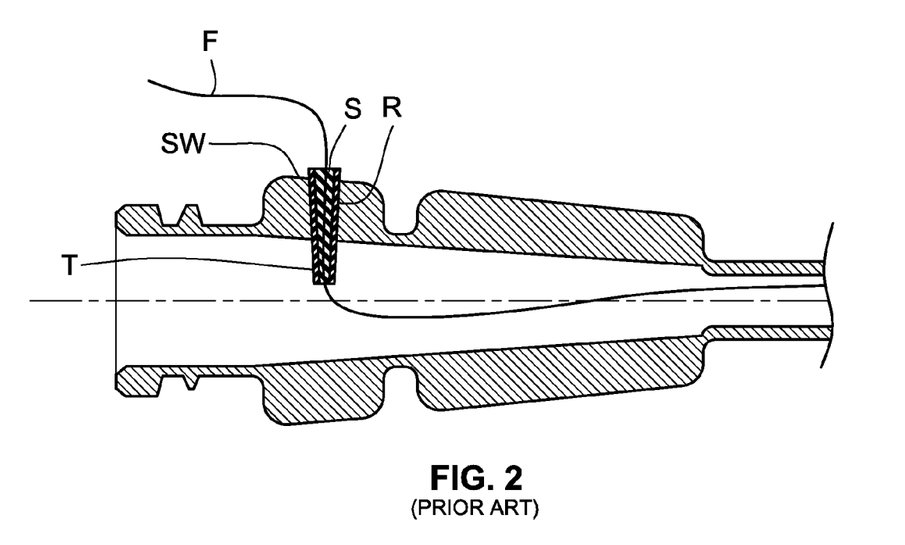

Another prior art locking catheter system believed to have been in the market since at least 1999 is sold under the SKATER® trademark by Angiotech Pharmaceutical (f.k.a. Medical Device Technologies, Inc.). A portion of the housing of this catheter is depicted in FIG. 2. As shown there, the housing of the SKATER catheter includes a seal recess R in the sidewall SW of the housing. A tube T is positioned in recess R and contains a deformable sealing material that fills the lumen of the tube. A flexible filament F passes through the deformable sealing material in order to limit system leakage as the suture passes through the recess.

Figure 3:
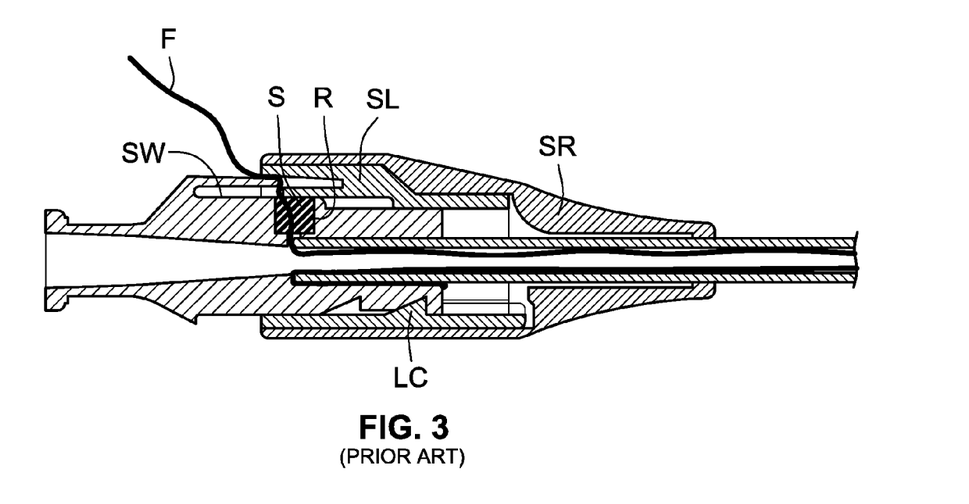

Yet another catheter anchoring system is described in U.S. Pat. No. 7,217,256. A significant problem associated with this system, which is illustrated in FIG. 3, is that the deformable sealing material that is located in the sidewall recess of the device may not, in fact, reliably seal. As can be seen in FIG. 3, a flexible filament F passes through sealing material S which is confined in a seal recess R in a sidewall SW of the housing of the device. As in the case of the other prior art locking catheter systems discussed above, leakage experienced with this device will be problematic because it can be unpleasant for the patient and, more importantly it can also create contamination risks for individuals who come in contact with the patient or the device.

Figure 4:
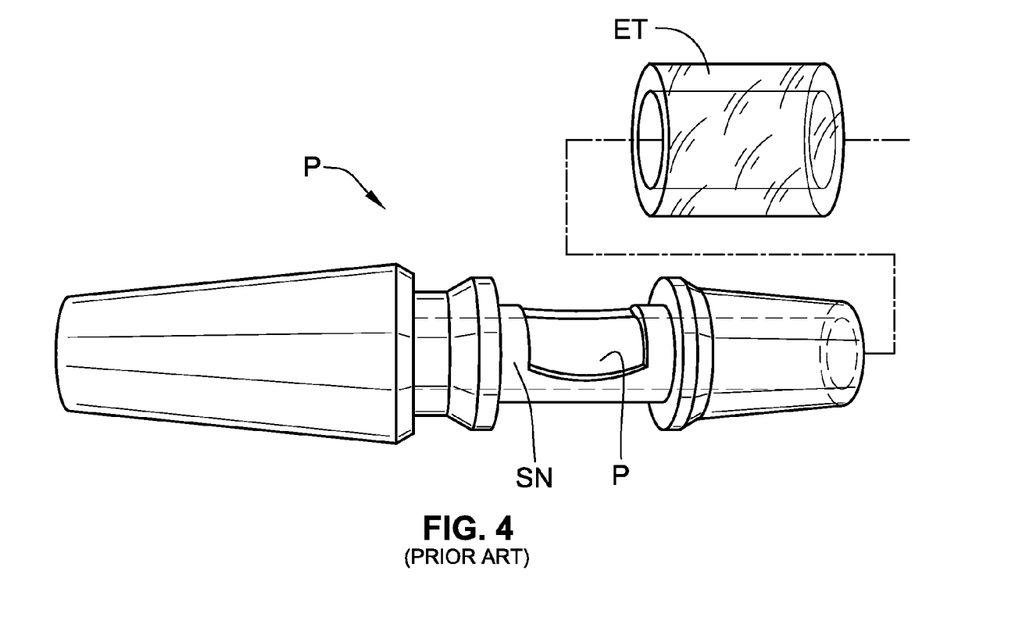

A medical device with a seal sleeve covering a port is shown in FIG. 4. This device is a urinary drainage bag having a sampling port P opening in the sidewall SW of the device and a piece of elastomeric tubing ET that fits over the port encircling and sealing the port when it is not in use. Sampling is carried out by passing a syringe needle through the tubing mounted over the port and withdrawing fluid. The elastomeric tubing maintains a seal against the syringe needle to prevent leakage. This device is believed to be first on market circa 1983.

Returning to FIG. 3, it is noted that the system of the '256 patent depicted there is also very difficult to unlock. To unlock the device, the user first needs to move a strain relief SR distally, which is difficult to accomplish because of the material of construction and the shape of the strain relief. Once the user moves the strain relief distally, he or she must simultaneously pry up the lock catch LC and move the slide SL distally. Given the size and shape of the lock catch, this maneuver is difficult and cumbersome to carry out.

In contrast, in the present catheter locking system, the user unlocks the system by simply depressing a latch and moving a locking slide distally which can be accomplished with one hand. Contoured surfaces on the locking slide make this maneuver particularly simple and efficient even when the user is wearing gloves and even if the gloves and slide surfaces are wet from bodily fluids.

Thus, prior art locking mechanisms are generally difficult to use. They are often less reliable than desired, may leak, and can be expensive to construct. Also, many have a high profile so that they stand away from the body and are inconvenient and uncomfortable to wear.

Additionally, many prior locking mechanisms lack a positive locking indication, leaving the physician uncertain as to whether or not the locking mechanism is fully and reliably engaged. Some prior locking mechanisms require a sealing compound to resist leakage from the catheter which may cause contamination or lead to failure of the seal. Finally, prior art locking mechanisms typically require two handed operation which make them unnecessarily difficult and cumbersome to use.

The present invention solves these problems by providing a locking mechanism that is easy to assemble, economical to manufacture, has a low profile, can be manipulated between its locked and unlocked positions with one hand, and includes a positive indication of when it is locked. The locking mechanism of the present invention also accommodates a range of different flexible filament diameters, provides a highly reliable seal without the use of sealing compounds to prevent leakage where the portion of the filament that controls the restraining portion of the catheter emerges from the catheter, and it includes a feature to facilitate storage of excess filament material when the filament is in its drawn-up restraining position.

SUMMARY OF THE INVENTION

The present invention comprises a leak-proof flexible filament controlled locking medical catheter. The catheter has a hollow flexible tube with a lumen, a flexible filament passing through the lumen, and at least one drainage or feeding hole in communication with the lumen. A restraining portion is located at the distal end of the flexible tube and is controlled by manipulating a free proximal control portion of the flexible filament.

A housing is located at the proximal end of the flexible tube. The housing has a lumen in fluid communication with the lumen of the flexible tube. A portion of the flexible filament resides in the lumen of the tube and the lumen of the housing and the proximal control portion of the flexible filament passes through an open port in the wall of the housing. The sidewall of the housing has a valley-shaped contour above the port and a resilient elastomeric cover on the sidewall contour and over the port, with a seal sleeve encircling the cover and the housing. The flexible filament which emerges from the open port passes through the cover and the interface established between the cover and the seal sleeve. The interface established between the elastomeric cover and the seal sleeve ensures a particularly effective fluid seal along the flexible filament. Thus, as the user pulls on or releases the free proximal control portion of the flexible filament to alter the state of the catheter control portion, the filament moves through the lumen of the tube, the lumen of the housing, the elastomeric cover and the interface between the elastomeric cover and the seal sleeve to provide a secure and reliable fluid-tight seal.

Although various locking mechanisms may be used in conjunction with the locking medical catheter described above, a particularly preferred locking mechanism is described in some detail below. This preferred locking mechanism relies upon spaced corresponding teeth between which the free proximal control portion of the flexible filament passes. Means are provided for moving the teeth into tight engagement for trapping the flexible filament therebetween and fixing it in place when the restraining portion of the catheter is in the desired position vis-à-vis the restraining portion of the catheter.

BRIEF DESCRIPTION OF THE DRAWINGS

The features of this invention that are believed to be novel are set forth with particularity in the appended claims. The invention, together with its objects and advantages, may be best understood with reference to the following description, taken in conjunction with the following drawings, in which like reference numerals identify like elements in the figures, and in which:

DESCRIPTION OF A PREFERRED EMBODIMENT OF THE INVENTION

Figure 5:
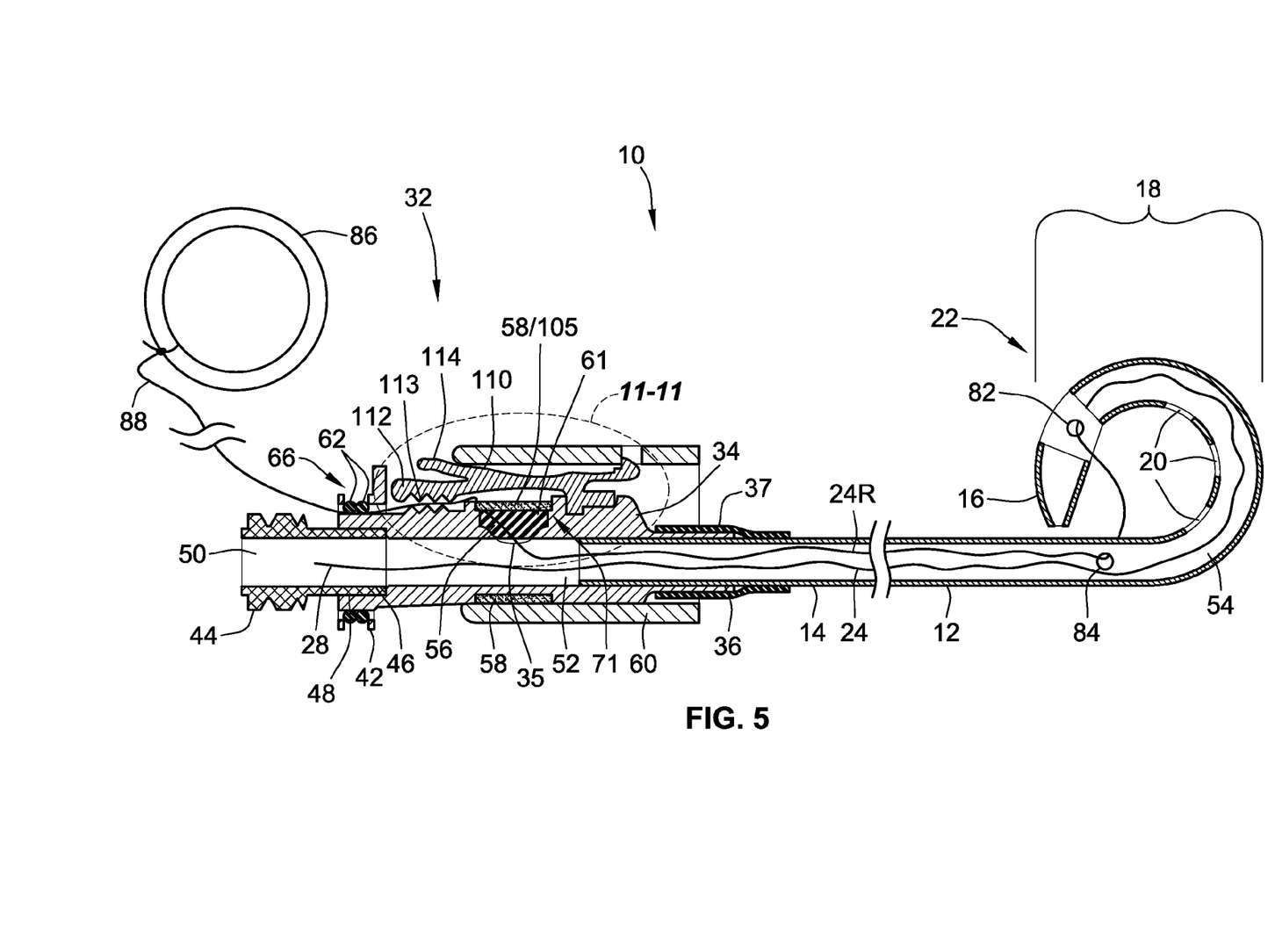
FIG. 5 is a section view of a locking medical catheter in accordance with the present invention.

Turning to FIG. 5, there is depicted a catheter 10 in accordance with the present invention, including a hollow flexible tube 12 with a proximal end 14, a distal end 16 and a restraining portion 18 at its distal end. The restraining portion of the tube includes at least one drainage (or feeding) hole 20 and, as shown, preferably a plurality of drainage (or feeding) holes. The hollow flexible tube may be made of polyurethane, polyethylene, EVA, nylon, or any other suitable flexible material acceptable for medical applications. The length of the tube, including restraining portion 18, may vary depending on the desired medical application.

As shown in the embodiment of the invention illustrated in FIG. 5, restraining portion 18 is in the form of a pigtail 22 which may be preformed at the distal end of the tube (as shown), so that the distal end forms this curved pigtail configuration when unstressed. The desired curve may be formed, for example, by heating the catheter tube while it is over a curved mandrel so that the tube will take on the shape of the mandrel when in its unstressed or resting position. Other preformed restraining configurations may be used, such as a J-curve or a malecot rib, or the restraining portion may be generally straight at rest until drawn into a curved locking configuration.

A locking mechanism 32 is also provided in accordance with the invention. The locking mechanism includes a housing 34 attached to the proximal end 14 of tube 12 of the catheter by gluing or by otherwise fixing the flexible tube inside nipple 36 of the housing. The gluing may be done using, for example, a cyanoacrylate compound that is coated 360° about the end of the tube before it is placed inside the nipple. Also, an optional stress relief sleeve 37 may be heat shrunk to the outside of the nipple and tube to minimize kinking. Housing 34 preferably will be molded from polycarbonate plastic or, alternatively, it may be made from other structural plastics such as ABS, polyurethane or nylon.

A luer lock 44 may be affixed to the proximal end of the housing with the distal nipple 46 of the luer lock seated in a receiving cavity 48 of the housing and sealed in place using an appropriate adhesive. The lumen 50 of the luer lock, the lumen 52 of the housing and the lumen 54 of the tube are all in communication to permit fluid to be conveyed through the catheter. Also, a flexible filament such as suture 24 is anchored with adhesive at the interface of the receiving cavity and the luer lock (or as otherwise desired) beyond the proximal end 14 of the tube at point 28 in the housing and is passed through lumen 54 of the tube. Preferably the flexible filament will be non-woven and non-porous and will be suture made from a suitable biocompatible material such as nylon. Luer lock 44 may be molded from polycarbonate plastic, or it may be made from other structural plastics such as ABS, polyurethane or nylon.

As can be seen in FIGS. 6-9, the sidewall 29 of the housing has a valley-shaped contour 31 extending across the top face 33 of the housing. The lumen 52 of the housing intersects this valley-shaped contour forming an open port 35 in outer wall 29 of the housing.

Figure 6A:
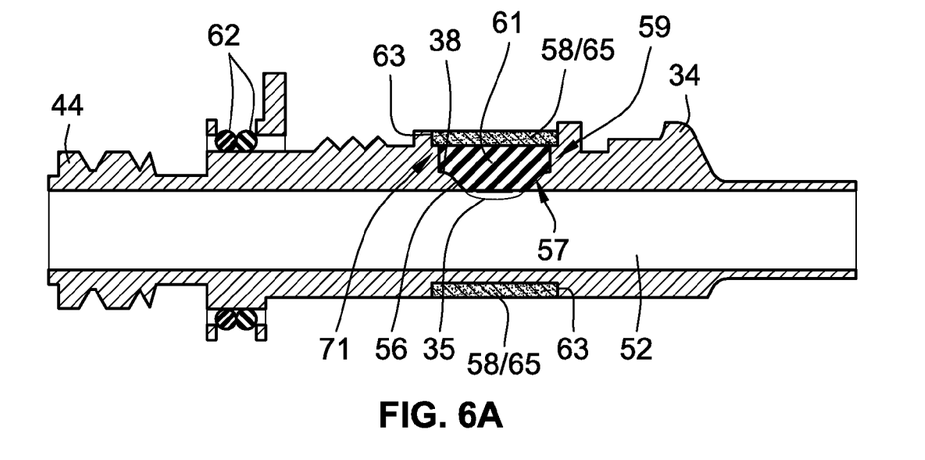
FIGS. 6A and 6B are partial section views of the housing portion of the medical catheter of FIG. 5, illustrating the overmolding of the elastomeric cover of the invention and the interface between the cover and a seal sleeve over the cover.
Figure 6B:
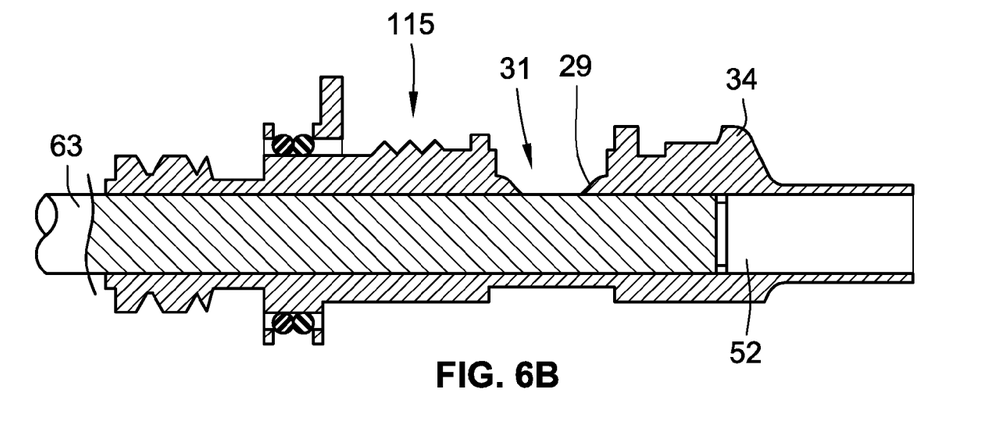
Figure 9:
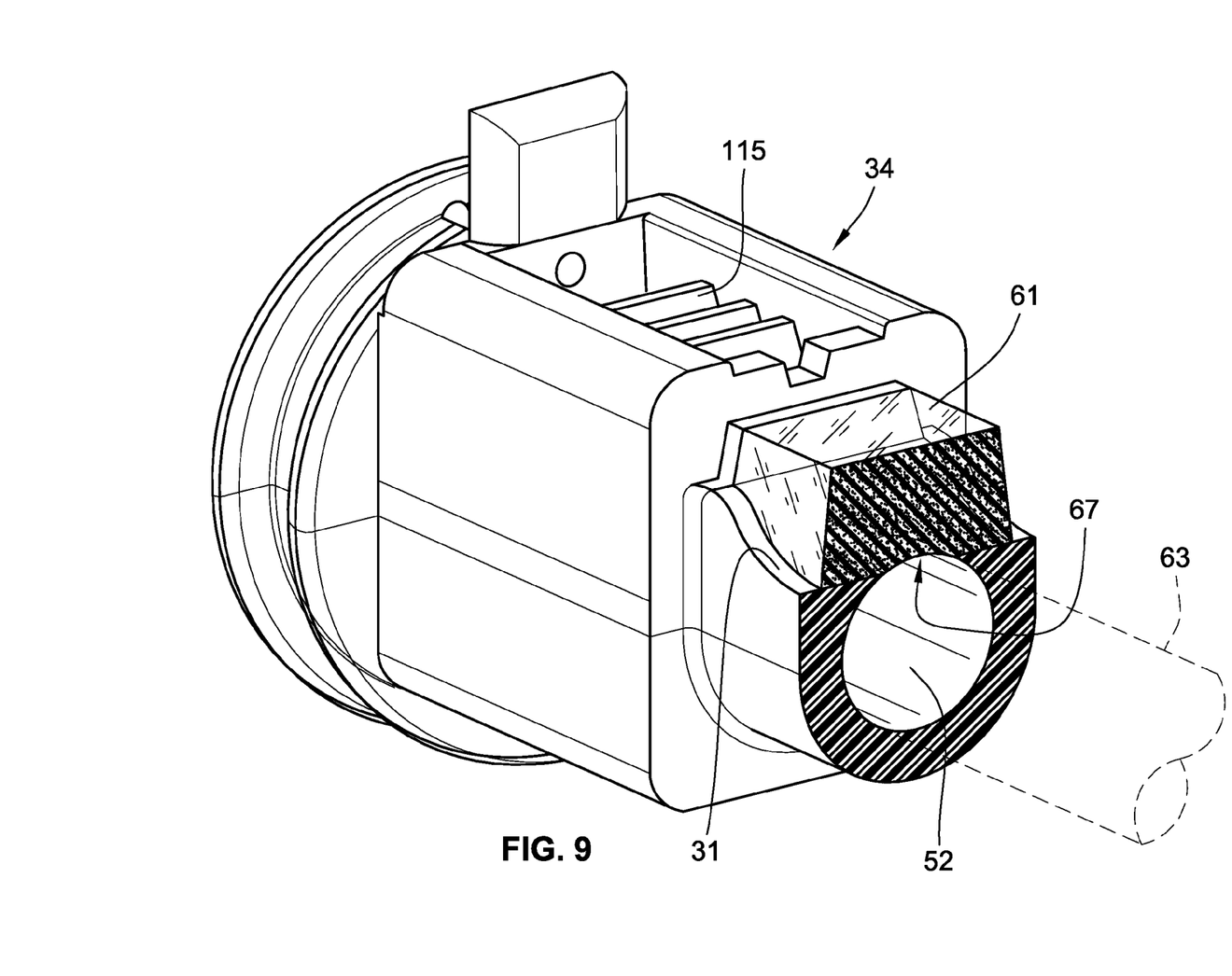
FIG. 9 is a section view of the housing portion of FIG. 8 taken along lines 9-9 of FIG. 8 through the elastomeric cover and the valley-shaped contour.
Figure 10:
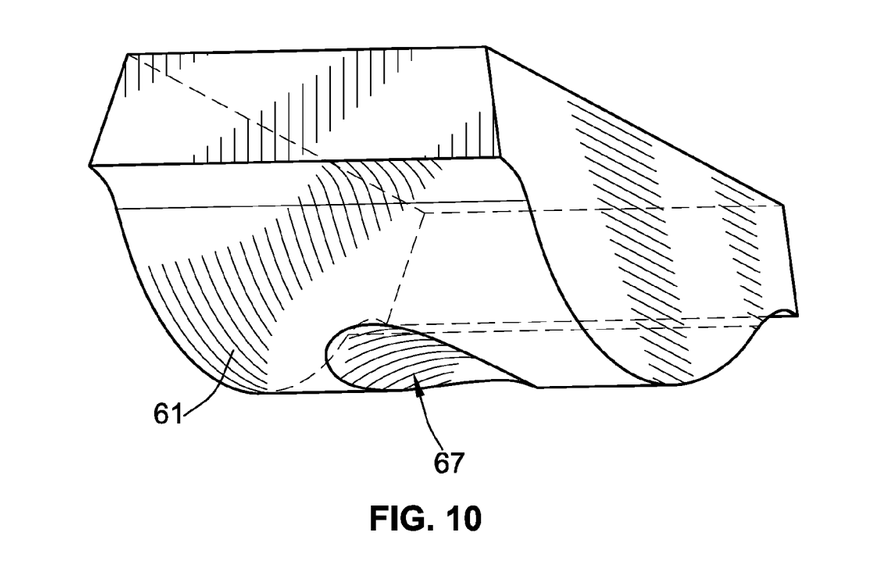
FIG. 10 is a perspective view of the elastomeric cover appearing in FIGS. 5, 6A, 8 and 9.

A resilient, elastomeric cover 61 (FIG. 10) extends across and covers valley-shaped contour 31, and is preferably formed by overmolding it in place. In order to prevent the elastomeric material of the cover from entering into open port 35 obstructing lumen 52 when the elastomeric cover is overmolded in place, a core pin 63 is positioned within housing lumen 52 during the overmolding process, as shown in FIGS. 6B. At the completion of the overmolding process, core pin 63 is removed. This process produces a slot 67 in the face of the elastomeric cover as best seen in FIG. 9. In a preferred embodiment, the cover material is silicone and possesses self-adhesive properties such that it permanently adheres to the outside of the housing along the valley-shaped contour. One currently preferred such silicone is SELECT-HESIVE™ KE2090-50AB which has a 50 A durometer. This material is available from Shincor Silicones, Inc. of Akron, Ohio.

A generally cylindrical, preferably extruded seal sleeve 58 (FIG. 6A) is mounted on the housing following the suture positioning process described below. Seal sleeve 58 may be made of a medical grade silicone or other suitable elastomeric material. Seal sleeve 58 fits snugly over and encircles the housing and cover 61 to insure that, during use of the device, fluids cannot pass through or around the interface 71 established between the cover and the sleeve or along the flexible filament. In an alternative embodiment, the suture may be passed through both elastomeric cover 61 as well as seal sleeve 58. In yet another alternative embodiment, the suture is passed through both elastomeric cover 61 and the heat shrinkable tube 65 described below for use in lieu of seal sleeve 58.

Seal sleeve 58 preferably rests in an annular slot 63 in the housing as shown. The resulting unexpectedly high resistance to leakage provided by the combination of the cover and seal sleeve is particularly useful when high pressures are generated within the lumen of the catheter such as when, for example, a physician attempts to unclog a catheter by injecting saline solution into the housing of the catheter. Optionally, a heat-shrinkable tube 65 may be used in place of elastomeric seal sleeve 58. If a heat-shrinkable tube is used, it preferably will be a thermoplastic, thin-walled tube made from PVC or other shrinkable material that shrinks upon application of a pre-determined heating temperature.

Figure 7:
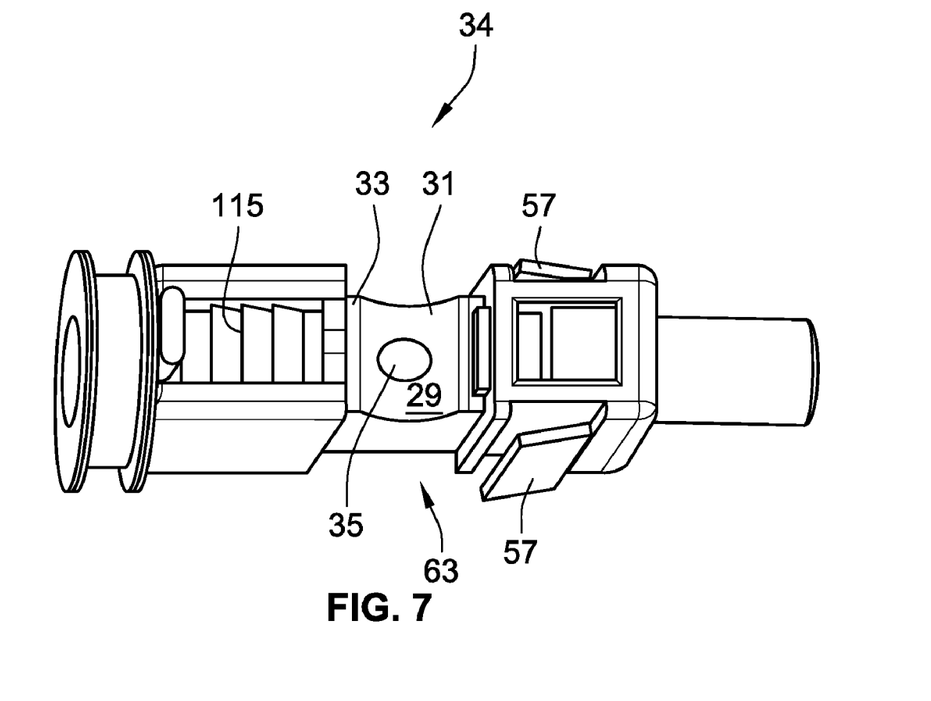
FIG. 7 is a perspective view of the housing portion of the medical catheter of FIG. 5.
Figure 8:
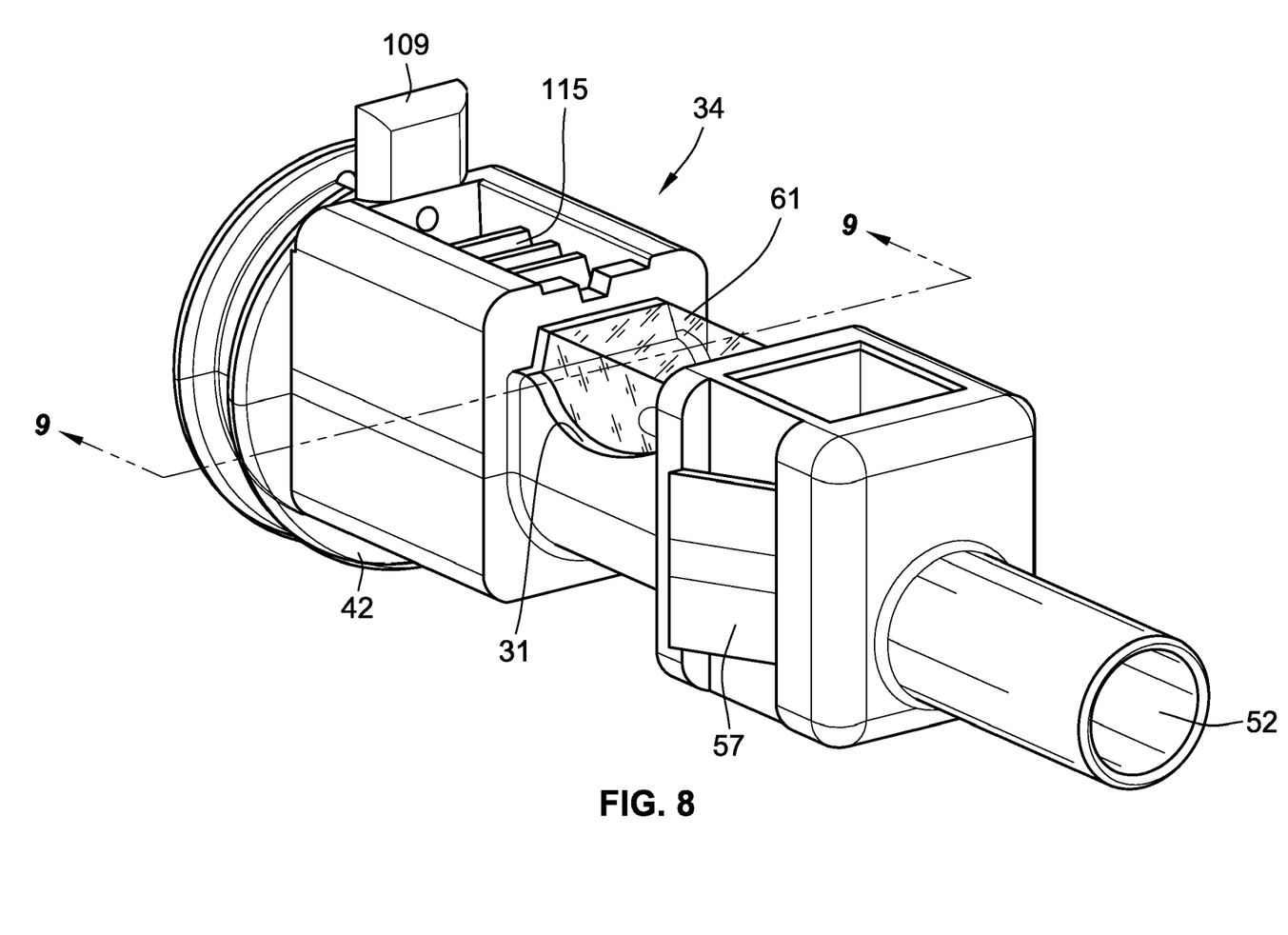
FIG. 8 is another perspective view of the housing portion of the medical catheter depicted in FIG. 5, showing the elastomeric cover over the valley-shaped contour in the sidewall of the catheter.

As best seen in FIG. 7, housing 34 may incorporate resilient proximally-directed locking wings 57 which may be molded with bottom clearance as shown to accommodate an inward spring action. When the annular locking slide 60 (see discussion below and FIG. 12) is mounted onto the housing, wings 57 engage slide undercut 73 (FIG. 12) to prevent the locking slide from detaching from the housing distally after the device is assembled.

Figure 11:
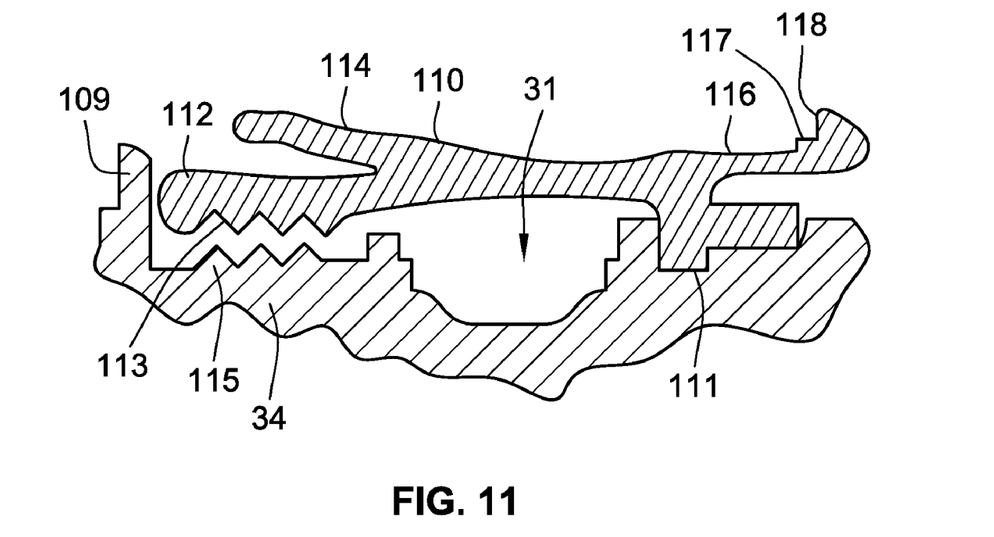
FIG. 11 is a section view, taken along section line 11-11 of FIG. 5, of the spring clamp feature and the portion of the housing of the medical catheter of FIG. 5 that retains the spring clamp.

Turning now to FIG. 11, a spring clamp 110 is shown in cross-section mounted onto housing 34. The spring clamp seats into the housing at annular channel 111 and is protected by a cover 109. Spring clamp 110 can be bonded to the housing at channel 111 with an appropriate bonding agent, but this is not mandatory since annular locking slide 60 (see below) will retain the clamp in position. The spring clamp includes a toothed section 112 with downwardly directed clamp teeth 113 for engaging corresponding upwardly directed housing teeth 115.

An integral pressure spring finger 114 is located on the spring clamp opposite the toothed section. Pressure spring finger 114 applies a clamping force to toothed section 112 during device use to cause the teeth of the spring clamp and the housing to tightly engage, trapping the flexible filament therebetween and fixing it in place. The spring clamp also incorporates a lock spring arm 116. A latch portion 118 of lock spring arm 116 engages locking surface 69 of slide 60 (FIG. 12) to removably lock the slide in place when the device is in the closed position.

Also, a clapper finger 117 may be included in lock spring 116 to create an audible click when the device is locked as the clapper finger strikes the undersurface of the slide. The click is produced because latch portion 118 flexes downwardly as the slide is pushed back and when it reaches surface 69 it springs up and hits the underside of the slide making an audible click sound. The audible click signals to the user that the device is, in fact, locked.

Spring clamp 110 may be molded from a polyimide plastic such as Ultem® plastic. Ultem plastic is available from SABIC Innovative Plastics in Pittsfield, Mass. Alternatively, it may be made from other structural plastics such as polycarbonate, polyurethane, nylon or Noryl® plastic. Noryl plastic is available also from SABIC Innovative Plastics.

Figure 12:
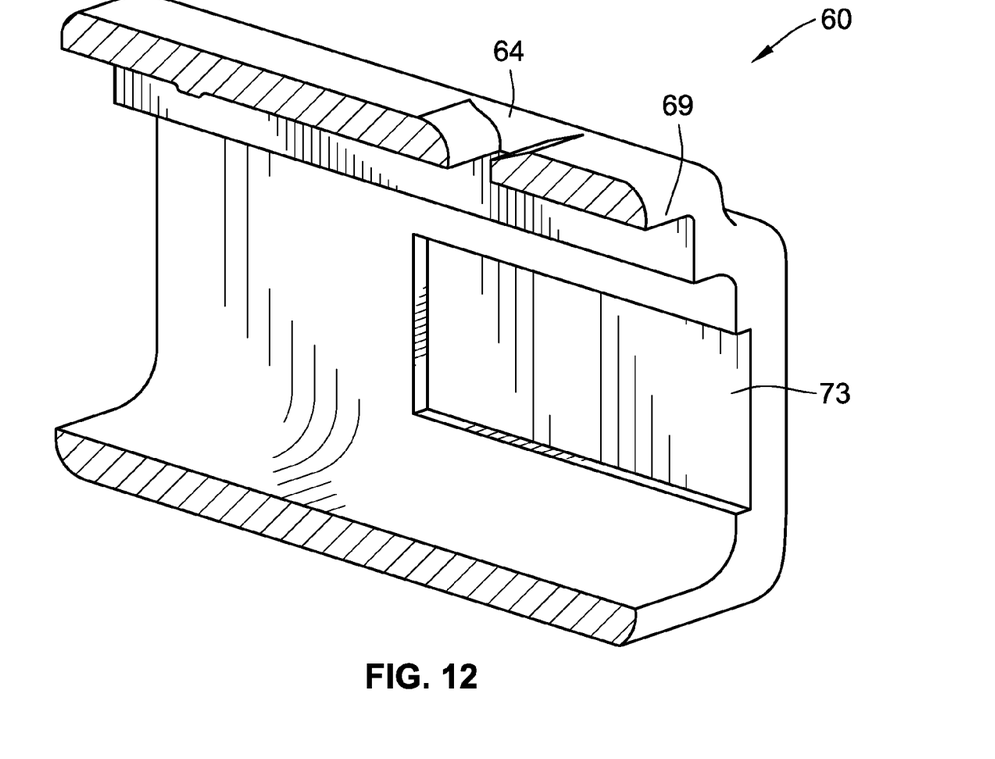
FIG. 12 is a partial cutaway perspective view of the annular locking slide of the medical catheter of FIG. 5.

An annular locking slide 60 as depicted, for example, in FIG. 12 is mounted for sliding movement on housing 34. Locking slide 60 is designed with an inner undercut 73. Undercut 73 together with locking wings 57 (FIG. 7) prevent the sleeve from detaching from the housing distally after the device is assembled, as explained above. Locking slide 60 also incorporates a storage stress relief undercut area 64. Latch portion 118 of the lock spring 116 (FIG. 11) resides in this stress relief area when, for example, the device is being stored in its package awaiting use by a physician. The storage stress relief area prevents the plastic of lock spring 116 from deforming and taking a set before it is used. Locking slide housing 60 may be molded from polycarbonate plastic, or it may be made from other structural plastics such as ABS, polyurethane or nylon. Locking mechanism 32 is in its "unlocked" configuration when the sleeve is in the position of FIG. 13A and in its "locked" configuration when the sleeve is in the position of FIG. 13B.

Referring back to FIG. 5, two O-rings 62 rest in a storage groove 66 adjacent the proximal end of the housing. The O-rings are preferably made of EPDM although they can be made from any acceptable elastomeric material. An annular collar 42 is molded onto the housing just distally of O-rings 62. The sliding movement of the sleeve is therefore limited such that it cannot move proximally beyond annular collar 42.

As discussed above and illustrated in FIG. 5, suture 24 is anchored at 28. The suture passes distally from this anchoring point through lumen 54 to a hole 82 near the distal end of tube 12 where it emerges from the tube and the returning portion 24R of the suture is passed back into the lumen through a more proximally positioned hole 84. The free proximal control portion 88 of the suture passes through lumen 54, open port 35, and cover 61, across the toothed section of the housing 113 and beyond the proximal end of the housing. Seal sleeve 58 is then placed over the suture-bearing cover to capture the suture in cover-to-seal sleeve interface 71. In an alternative embodiment, the suture is passed through the interface between cover 61 and a heat shrinkable tube 65 that is "heat shrunk" in place and used instead of seal sleeve 58, as described previously.

Figure 13A:
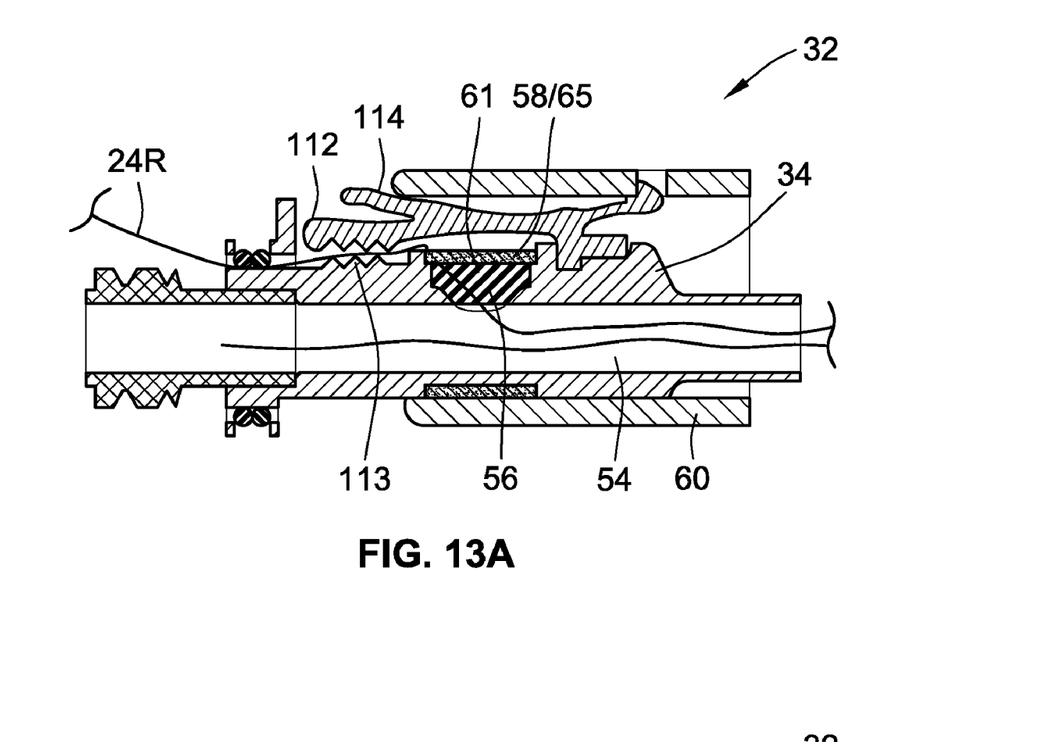
FIGS. 13A and 13B are partial cutaway plan views of the locking mechanism of the medical catheter of FIG. 5 with the annular locking sleeve respectively in the "opened" and "closed" positions.
Figure 13B:
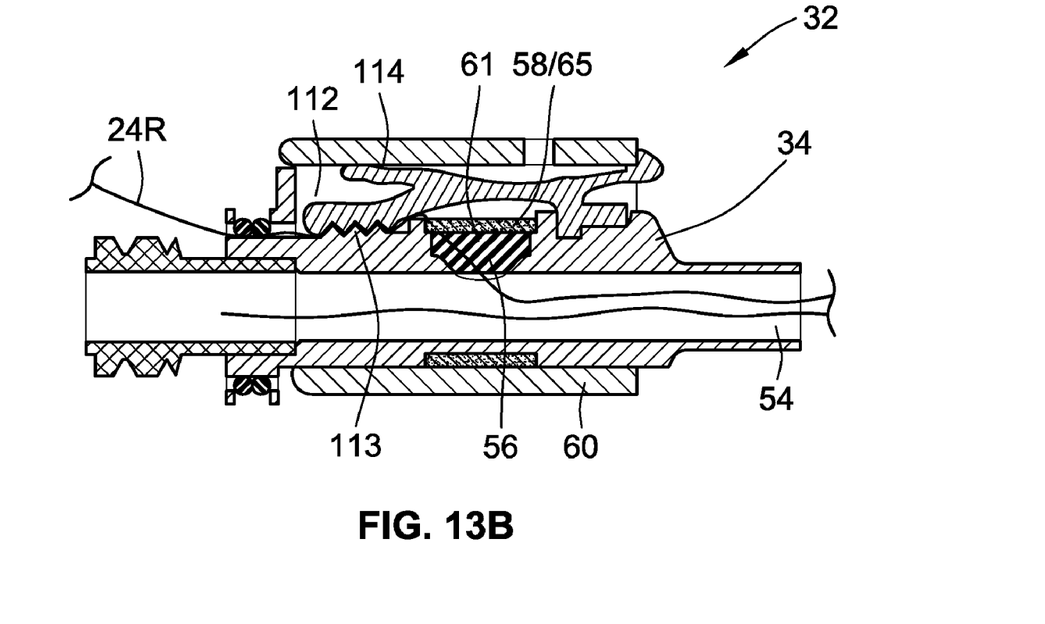

Suture 24 is free to slide proximally or distally including through cover 61 and cover-to-seal sleeve interface 71 so long as the locking mechanism is in the "unlocked" position of FIG. 13A. The resilient and elastomeric characteristics of the cover and seal sleeve (or the heat shrinkable tube) ensure a gas and liquid seal about the surface of the suture both as it is moved back and forth through flexible tube 12 and when the device and the suture are locked in position. In one alternative embodiment, the suture is passed through cover 61 and the interface between the cover and the heat shrinkable tube 65 described previously for use in lieu of seal sleeve 58.

Figure 14A:
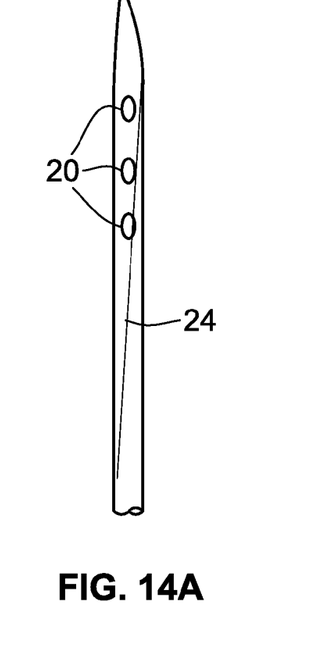
FIGS. 14A and 14B are views of the distal restraining portion of the locking medical catheter of FIG. 5 showing respectively a straight configuration with, e.g., a cannula is positioned within the lumen of the tube, and a closed and locked pigtail restraining configuration.
Figure 14B:
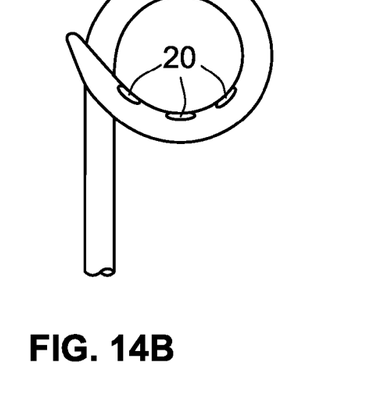

Referring again to FIG. 5, a ring 86 may be attached to the proximal end 88 of the suture to facilitate grasping the free proximal control portion of the suture to draw it through the cylindrical tube thereby placing restraining portion 18 in the constraining configuration of FIGS. 5 and 14B before locking the suture and hence the restraining portion in place. Once the catheter is locked in this configuration, excess suture may be stored in storage groove 66 by winding the free proximal control portion of the suture into the spaces next to and/or between the O-rings 62. Ring 86 can be cut off and discarded after the suture is stored by cutting the suture below the ring. If the physician does not desire to store the excess suture after the device is placed in its fully locked position, the suture can simply be cut close to luer lock 44 without using storage groove 66.

Figure 15:
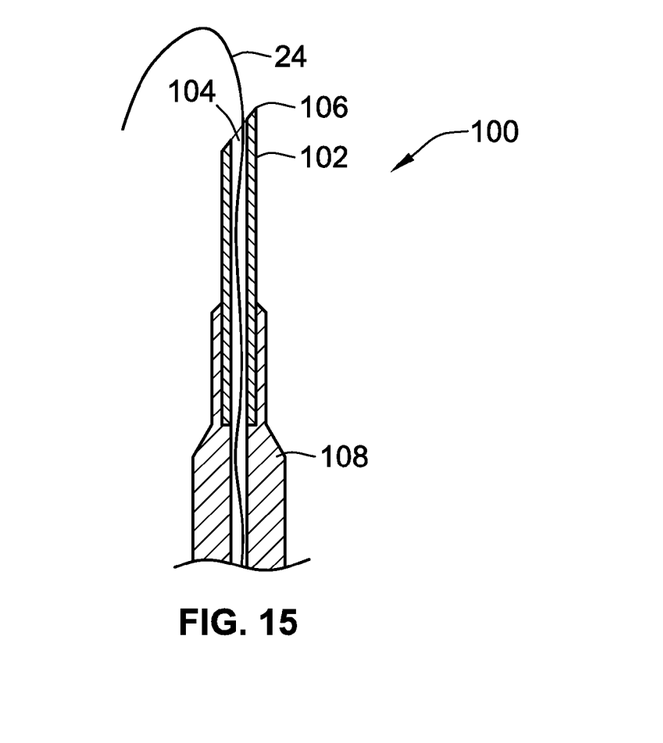
FIG. 15 is a cutaway elevation view of a hollow needle that may be used for passing a flexible filament through the elastomeric cover appearing in FIGS. 5, 6A, 8 and 9.

A particularly effective process for passing suture 24 through cover 61 entails the use of a hollow needle (FIG. 15). One such needle 100 having a cannula 102, a needle channel 104, a beveled tip 106 and a base 108 is shown in FIG. 15. Grasping the base 108 of the needle, the installer may pass needle cannula 102 through cover 61, then feed suture through channel 104 and out past the needle tip. Finally, separately grasping base 108 and suture end 24R, the installer removes the cannula from cover 61, so that the suture remains embedded within and passing through the cover.

The locking medical catheter of the invention may be used as follows:

1. Drainage and insertion sites are selected and prepared using appropriate known techniques and a guidewire is inserted into the drainage site. (Note: This description describes the "over-the-guidewire" introduction technique. Some physicians also use a "direct puncture" technique in some circumstances. This invention is equally useful when performing the direct puncture technique where a trocar is used in place of the guidewire. The locking mechanism is identical for both catheter introduction methods).

2. A catheter in accordance with FIG. 5 (or otherwise in accordance with the invention) is provided with locking mechanism 32 in the unlocked position of FIG. 13A.

3. A cannula (not shown) is then inserted into tube 12 of the catheter to maintain restraining portion 18 of the tube in a straight configuration (FIG. 14A) so that the catheter may be passed over the previously emplaced guidewire into the drainage site while monitoring using non-invasive imaging such as fluoroscopy, CT (computed tomography) or ultrasound to ensure that restraining portion 18 is properly positioned within the cavity. The proximal end of the catheter including the locking mechanism will be outside of the patient's body close to the skin surface at the entry point into the body. At this point, the cannula and guidewire are removed.

4. When the cannula is removed, the restraining portion of tube 12 curls into its preformed unstressed pigtail configuration (FIG. 5). The physician then pulls upon suture 24 drawing it through resilient cover 61 to remove any slack and optionally to further curl the pigtail (FIG. 14B).

5. Locking slide 60 is then moved proximally to its locked position (FIG. 13B), compressing pressure spring 114 to maintain the toothed section on the spring clamp 112 in engagement with the toothed section on the housing 113 thereby trapping the suture between the two toothed surfaces. Additionally, when the proximally moving slide housing 60 reaches collar 42 (in the locked position of the device) lock spring 116 causes latch 118 to move upwardly and to engage distal locking surface 65 of slide 60 thereby fixing the device in the locked position. Simultaneously with this, clapper finger 117 on the lock spring strikes the underside of slide 60 creating an audible click. This click signals to the physician that the device is in its fully locked position.

6. If desired, excess suture may be wound onto the housing and removably retained in and among the spaces between the O-rings 62 and groove 66 in which the O-rings are mounted, and then ring 86 may be cut away. If the physician does not desire to store the suture in this manner, the suture is simply cut close to the housing after the device is locked.

7. Luer lock 44 is then attached to an appropriate drainage collection system and fluid is drained as appropriate.

8. Once the drainage procedure is completed and the catheter is to be removed, the drainage device is disconnected from the catheter. If suture was stored using the O-rings and groove 66, the suture is unwound. Latch 118 is then depressed to release the locking slide 60, and the slide is moved to the unlocked (distal) position. This slide movement releases the spring clamp and, hence the suture and retention feature, and the catheter may now be removed from the cavity.

9. A like procedure can be used when the locking catheter is to be used for feeding purposes.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What we claim is:

1. A flexible filament controlled locking medical catheter comprising:
   a hollow flexible tube having a lumen, a flexible filament passing through the lumen, and at least one drainage or feeding hole in communication with the lumen;
   a restraining portion at the distal end of the flexible tube controlled by a free proximal control portion of the flexible filament; and
   a housing at the proximal end of the flexible tube, the housing having a lumen in fluid communication with the lumen of the flexible tube,
   the housing having a port opening in the sidewall of the housing and communicating with the housing lumen, a contour over the port, and an elastomeric cover in the contour, positioned against the port opening to present elastomeric material at the port opening; and
   a seal sleeve encircling the housing and positioned over the cover establishing an interface between the elastomeric cover and the seal sleeve,
   the flexible filament passing through the lumen of the tube, through the lumen of the housing, through the portion of the elastomeric cover positioned against the port, and through the interface, to present the proximal control portion of the flexible filament at the proximal end of the catheter.

2. The medical catheter of claim 1 in which the restraining portion is a preformed pigtail configuration.

3. The medical catheter of claim 1 in which the sidewall of the housing has a valley-shaped contour over the port and the cover fills the contour.

4. The medical catheter of claim 1 in which the cover is made of silicone having self-adhesive property and adheres to the contour.

5. The medical catheter of claim 1 in which the seal sleeve is made of a medical grade silicone.

6. The medical catheter of claim 1 in which the seal sleeve encircles the housing and the elastomeric cover.

7. The medical catheter of claim 1 in which the flexible filament passes through the seal sleeve instead of the interface.

8. The medical catheter of claim 1 in which a heat-shrinkable tube is used as the seal sleeve.

9. The medical catheter of claim 8 in which the heat-shrinkable tube is a thermoplastic, thin-walled tube made from PVC.

10. The medical catheter of claim 8 in which the flexible filament passes through the heat-shrinkable tube instead of the interface.

11. The medical catheter of claim 1 in which the housing is provided with a locking mechanism to lock the flexible filament in position.

12. The medical catheter of claim 11 in which the locking mechanism comprises spaced corresponding toothed sections between which the flexible filament passes and means for moving the teeth of the toothed sections into tight engagement to fix the flexible filament in place.

13. The medical catheter of claim 12 in which the housing is provided with upstanding teeth and a spring clamp is mounted on the housing and provided with downwardly directed teeth for engaging the housing teeth.

14. The medical catheter of claim 13 including a pressure spring for applying force to the spring clamp when the locking mechanism is in its locked configuration.

15. The medical catheter of claim 14 in which the locking mechanism includes a locking slide for urging the teeth into tight engagement, the locking slide having a locking surface, and the spring clamp includes a lock spring arm having a latch portion for engaging the locking surface of the slide to removably lock the slide housing in place.

16. The medical catheter of claim 15 in which the latch portion includes a clapper finger for striking the slide to produce an audible click when the device is locked.

17. The medical catheter of claim 15 in which the slide housing has a stress relief clearance area for storing the lock spring arm in an unstressed configuration before use of the locking medical catheter.

18. The medical catheter of claim 1 in which the housing has a groove on its outer surface holding at least two elastomeric O-rings in abutment to receive and removably retain the proximal control portion of the flexible filament.

19. A flexible filament controlled locking medical catheter comprising:
   a hollow flexible tube having a lumen, a flexible filament passing through the lumen, and at least one drainage or feeding hole in communication with the lumen;
   a restraining portion at the distal end of the flexible tube controlled by a proximal control portion of the flexible filament; and a housing at the proximal end of the flexible tube, the housing having a lumen in fluid communication with the lumen of the flexible tube, the housing having a port opening in the sidewall of the housing and communicating with the housing lumen, a contour over the port, and an elastomeric cover in the contour, positioned against the port opening to present elastomeric material at the port opening; and a seal sleeve over the cover establishing an interface between the elastomeric cover and the seal sleeve, the flexible filament passing through the lumen of the tube, through the lumen of the housing, through the portion of the elastomeric cover positioned against the port, and through the interface, to present the proximal control portion of the flexible filament at the proximal end of the catheter; and a locking mechanism to fix the flexible filament in position comprising spaced corresponding toothed sections between which the proximal control portion of the flexible filament passes and means for moving the teeth of the toothed sections into tight engagement to lock the flexible filament in place.

20. The medical catheter of claim 19 in which the housing is provided with upstanding teeth and a spring clamp is mounted on the housing and provided with downwardly directed teeth for engaging the housing teeth.

* * * * *